US009636217B2

(12) United States Patent
Kunte (10) Patent No.: US 9,636,217 B2
(45) Date of Patent: May 2, 2017

(54) EQUIPMENT AND METHODS USED IN FOLDING AND IMPLANTING FOLDABLE LENSES IN THE EYE (71) Applicant: Novartis AG, Basel (CH)

(72) Inventor: Neelesh Kunte, Arlington, TX (US)

(73) Assignee: Novartis AG, Basel (CH)

( * ) Notice: Subject to any disclaimer, the term of this patent is extended or adjusted under 35 U.S.C. 154(b) by 223 days.

(21) Appl. No.: 14/273,279

(22) Filed: May 8, 2014

(65) Prior Publication Data
US 2015/0320593 A1 Nov. 12, 2015

(51) Int. Cl.
A61F 9/007 (2006.01)
A61F 2/16 (2006.01)

(52) U.S. Cl.
CPC .......... A61F 2/1678 (2013.01); A61F 2/1662 (2013.01); A61F 2/1691 (2013.01)

(58) Field of Classification Search
CPC ........ A61F 9/00; A61F 9/007; A61F 9/00736; A61F 2/1662–2/1678; A61F 2/169; A61F 2/16–2/18
See application file for complete search history.

(56) References Cited

U.S. PATENT DOCUMENTS

| 4,747,404 A | 5/1988 | Jampel et al. |
| 4,819,631 A | 4/1989 | Poley |
| 5,304,182 A | 4/1994 | Rheinish et al. |
| 5,354,333 A | 10/1994 | Kammann et al. |
| 5,468,246 A | 11/1995 | Blake |
| 5,653,753 A | 8/1997 | Brady et al. |
| 5,702,400 A | 12/1997 | Brown et al. |
| 5,702,402 A | 12/1997 | Brady |
| 5,711,317 A | 1/1998 | McDonald |
| 5,772,667 A * | 6/1998 | Blake ................ A61F 2/1662 606/107 |
| 6,283,976 B1 | 9/2001 | Portney |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,428,545 B2 | 8/2002 | Portney |
| 6,500,181 B1 | 12/2002 | Portney |
| 6,786,911 B2 | 9/2004 | Mitomo et al. |
| 7,074,227 B2 | 7/2006 | Portney |
| 7,104,996 B2 | 9/2006 | Bonutti |
| 7,422,604 B2 | 9/2008 | Vaquero et al. |

(Continued)

OTHER PUBLICATIONS

International Search Report and Written Opinion of the International Searching Authority for PCT/US2015/029859, 6 pages, dated Aug. 10, 2015.

Primary Examiner — Shaun L David
(74) Attorney, Agent, or Firm — Darien Reddick (57) ABSTRACT Apparatuses, systems, and methods for folding an intraocular lens and inserting an intraocular lens into an eye are disclosed herein. In some instances, a system for folding an intraocular lens may include a folding pin, a guide pin rotatable about a longitudinal axis of the folding pin, and a stage laterally moveable relative to the folding pin. An intraocular lens may be secured between the folding pin and the guide pin and be folded onto the folding pin during rotation of the guide pin. A retention member may be used to hold the folded intraocular lens onto the folding pin.

8 Claims, 6 Drawing Sheets (56) References Cited

U.S. PATENT DOCUMENTS

| | | |
|---|---|---|
| 7,429,263 B2 | 9/2008 | Vaquero et al. |
| 7,476,229 B2 | 1/2009 | Meyer |
| 2008/0033449 A1 | 2/2008 | Cole et al. |
| 2009/0204122 A1 | 8/2009 | Ichinohe et al. |

\* cited by examiner

EQUIPMENT AND METHODS USED IN FOLDING AND IMPLANTING FOLDABLE LENSES IN THE EYE

TECHNICAL FIELD

The present disclosure relates to systems, apparatuses, and methods for folding an intraocular lens ("IOL") and implanting an IOL into an eye.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An insertion cartridge of an IOL injector is loaded with the IOL, the tip of the insertion cartridge is inserted into the incision, and the lens is delivered into the eye.

SUMMARY

According to one aspect, the disclosure describes an intraocular lens folding system that may include a folding device. The holding device may include a body, a folding pin mounted to the body, a guide pin mounted to the body adjacent to the folding pin, and a stage mounted to the body adjacent to the folding pin. The stage may be laterally moveable relative to the folding pin. The guide pin may be rotatable on the body about a longitudinal axis of the folding pin.

Another aspect of the disclosure encompasses a method of folding an intraocular lens that may include positioning a portion of an intraocular lens between a folding pin and a guide pin and rotating the guide pin about the folding pin to cause the intraocular lens to be folded on the folding pin.

The various aspects may include one or more of the following features. A folding pin may be rotatable relative to the body about the longitudinal axis. The folding pin may be removable from the body. The guide pin and folding pin may be configured to rotate synchronously. A rate at which the guide pin rotates and the rate at which the folding pin rotates may be the same. Lateral movement of the stage may be synchronized with the rotation of the guide pin. A speed of the lateral movement of the stage may be the same as a tangential velocity of the guide pin. A folding system may also include an insertion device. The insertion device may include a housing and a plunger moveable within the housing. A distal end of the plunger may be configured to receive at least a portion of the folding pin.

The various aspects may also include one or more of the following features. An intraocular lens may be disposed on a stage. The stage may be moved in a lateral direction relative to the folding pin. Moving the stage in a lateral direction relative to the folding pin may include moving the stage in a lateral direction at a speed that is substantially the same as a speed at which the intraocular lens is removed from the stage during rotation of the guide pin about the folding pin. The guide pin may be rotated a defined angular amount. The guide pin may be retracted after the guide pin has rotated the defined angular amount. A binding member may be applied to the intraocular lens upon complete folding of the intraocular lens. The folding pin may be removed with the folded intraocular lens disposed thereon.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

The present disclosure is directed to systems, methods, and apparatuses for folding an IOL. More particularly, the present disclosure describes systems, methods, and apparatuses directed to folding an IOL prior to implantation into an eye.

Figure 1:
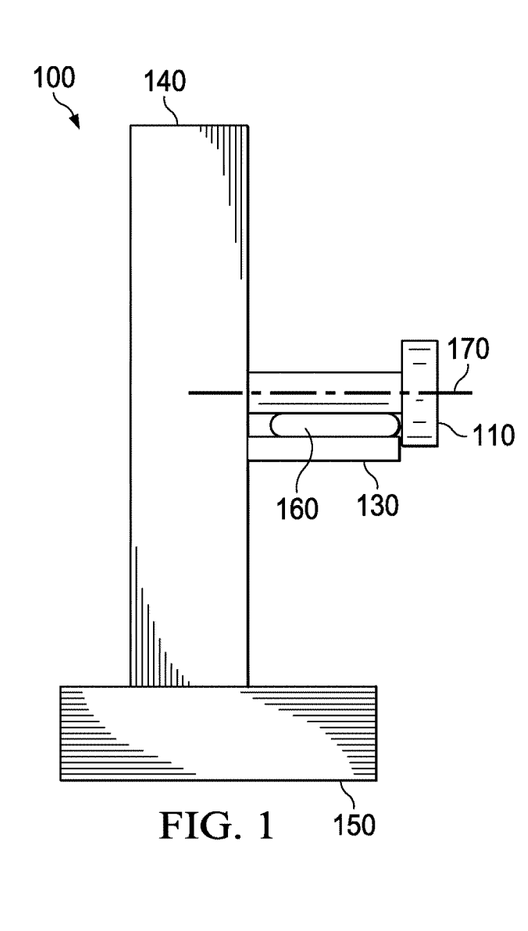
FIGS. 1 and 2 show a side view and a front view, respectively, of an example intraocular lens folding device.
Figure 2:
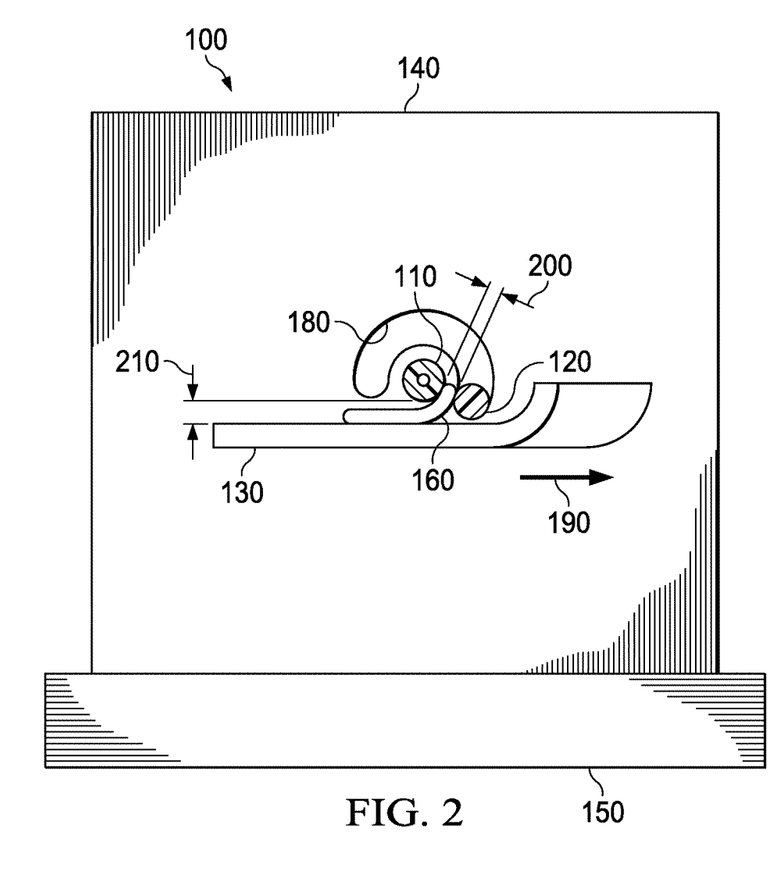

FIG. 1 shows a side view of an example IOL folding device 100. The device 100 includes a folding pin 110, a guide pin 120, a stage 130, a back 140, and a base 150. FIG. 2 shows a front view of the IOL folding device 100 in which the folding pin 110 and guide pin 120 are shown in cross-section. An IOL 160 is also shown on the stage 130.

In some implementations, one or both of the folding pin and guide pin, such as folding pin 110 and guide pin 120 as well as the other example folding pins and guide pins described herein, may have a surface texture. The surface texture may be adapted to grip an IOL during folding. In other instances, one or both of the folding pin and guide pin may include one or more grooves or serrations formed therein. The serrations and/or grooves may also be adapted to grip an IOL during folding.

The guide pin 120 is moveable about the folding pin 110 along a path 180. Particularly, in some implementations, the path 180 may be an arcuate path. For example, the path 180 may be a circular path. The path 180 may define an arcuate path such that the guide pin 120 is rotatable about a central longitudinal axis 170 of the folding pin 110. In other implementations, the path 180 may define a course such that the guiding pin 120 may be offset from the central longitudinal axis 170. Further, in some implementations, the course defined by path 180 may cause the guiding pin 120 to move in a circular rotation about the folding pin 110. In other implementations, the shape defined by the path 180 may cause the guide pin 120 to move about the folding pin 110 in a non-circular path. For example, in some instances, the path 180 may define an elliptical, a decreasing-radius curvature, an increasing-radius curvature, or define any other desired path.

In some instances, the folding pin 110 may rotate about the longitudinal axis 170 as the guide pin 120 moves along path 180. For example, in some instances, the folding pin 110 and the guide pin 120 may move at the same angular speed. In some implementations, the folding pin 110 and the guide pin 120 may move at different angular speeds. For example, in some instances, the angular speed of the folding pin 110 may be higher than the angular speed of the guide pin 120. In other instances, the angular speed of the folding pin 110 may be less than the angular speed of the guide pin 120.

The stage 130 may be moveable relative to folding pin 110. In some instances, the stage 130 moves horizontally in the direction of arrow 190. In other instances, movement of the stage 130 may have a vertical component. That is, in some instances, the stage 130 may have an inclined or declined movement when feeding the IOL to the folding pin 110 and guide pin 120. For the example device 100 shown in FIGS. 1 and 2, the stage 130 moves horizontally in the direction of arrow 190 to feed IOL 160 to the folding pin 110 and guide pin 120.

In operation, the IOL 160 may be placed on the stage 130 and clamped or otherwise held between the folding pin 110 and guide pin 120. The folding pin 110, guide pin 120, and stage 130 may begin moving in their respective paths. Particularly, the folding pin 110 rotates about longitudinal axis 170, and the guide pin 120 moves about the path 180. In the example of FIG. 1, the path 180 forms an arcuate path that has a constant radial offset from the longitudinal axis 170. Thus, a gap 200 formed between the folding pin 110 and the guide pin 120 is substantially constant throughout the folding process of the IOL 160. In some instances, the gap 200 formed between the guide pin 120 and the folding pin 110 may be the thickness of IOL 160. In some instances, the size of gap 200 may be less than the thickness of IOL 160. In other instances, the size of gap 200 may be larger than the thickness of IOL 160.

As the folding pin 110 rotates and the guide pin 120 moves about path 180, the stage 160 moves in the direction of arrow 190 to "feed" the IOL 160 as the IOL 160 is folded on the folding pin 110. In addition, the stage 130 is positioned relative to the folding pin 110 such that, as the folding occurs, the stage 130 maintains the IOL 160 against the folding pin 110. For example, in some instances, a gap 210 formed between the stage 130 and the folding pin 110 may be the thickness of IOL 160. In some instances, the size of gap 210 may be less than the thickness of IOL 160. In other instances, the size of gap 210 may be larger than the thickness of IOL 160.

FIGS. 3A-3E illustrate an example folding process. Particularly, FIGS. 3A-3E may illustrate folding of IOL 160 by device 100, although only the folding pin 100, guide pin 120, stage 130, IOL 160, and path 180 are shown. This series of figures, for example, illustrates movement of movement of the guide pin 120 about the folding pin 110 to maintain the IOL 160 against the folding pin 110 as the IOL 160 is folded. Further, as also shown in FIGS. 3A-3E, the stage 130 moves laterally to both feed the IOL 160 during folding as well as maintain the IOL 160 against the folding pin 110. In some instances, the stage 130 may have a speed that is the same or substantially the same as the tangential velocity of the folding pin 110. In some instances, the stage 130 may have a speed that is the same or substantially the same as the tangential velocity of the guide pin 120. In other instances, the speed of the stage 130 may be the same speed at which the IOL 160 is removed from the stage 130 by folding of the IOL 160 by the folding pin 110 and guide pin 120.

Figure 3A:
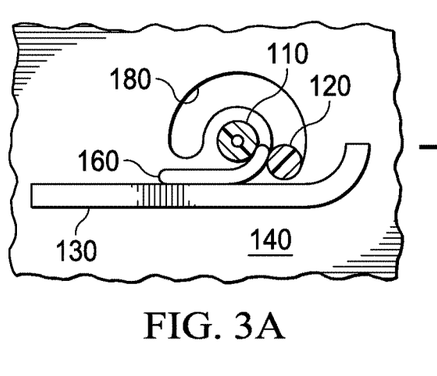
FIGS. 3A-3E illustrates an example folding operation performed by the intraocular lens folding device of FIGS. 1 and 2.
Figure 3B:
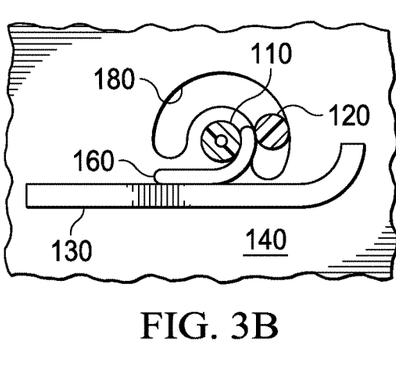
Figure 3C:
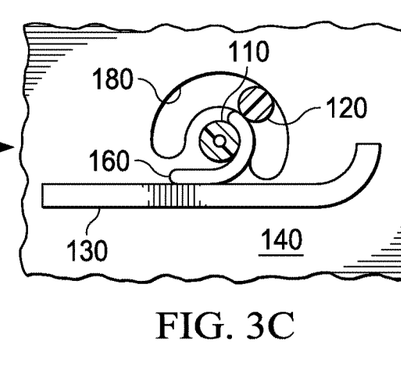
Figure 3D:
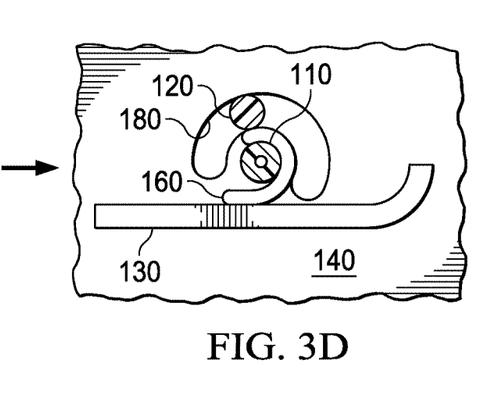
Figure 3E:
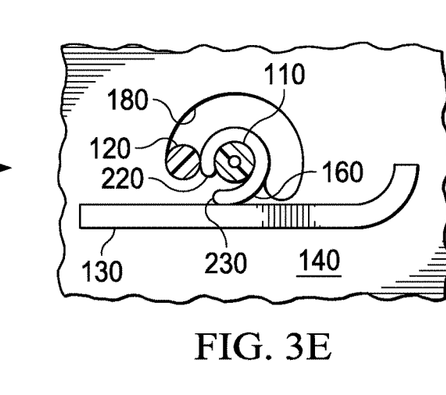

FIG. 3E shows the IOL 160 in a folded condition on the folding pin 110. As shown, a leading end 220 of the IOL 160 may be lie under a tailing end 230 of the IOL 160. Although FIG. 3E shows that the tailing end 230 of the IOL 160 slightly overlapping the leading end 220, this is provided merely as an example. In some instances, a portion of the IOL 160 may overlap significantly more of itself when in a completely folded condition. For example, during the folding process shown in FIGS. 3A-3E, the folding pin 110 and guide pin 120 may rotate approximately 180°. However, in other implementations, the folding pin 110 and the guide pin 120 may rotate more than 180°. In such instances, the folding device may include a plurality of guide pins 120.

Figures 4, 5, 6, 7:
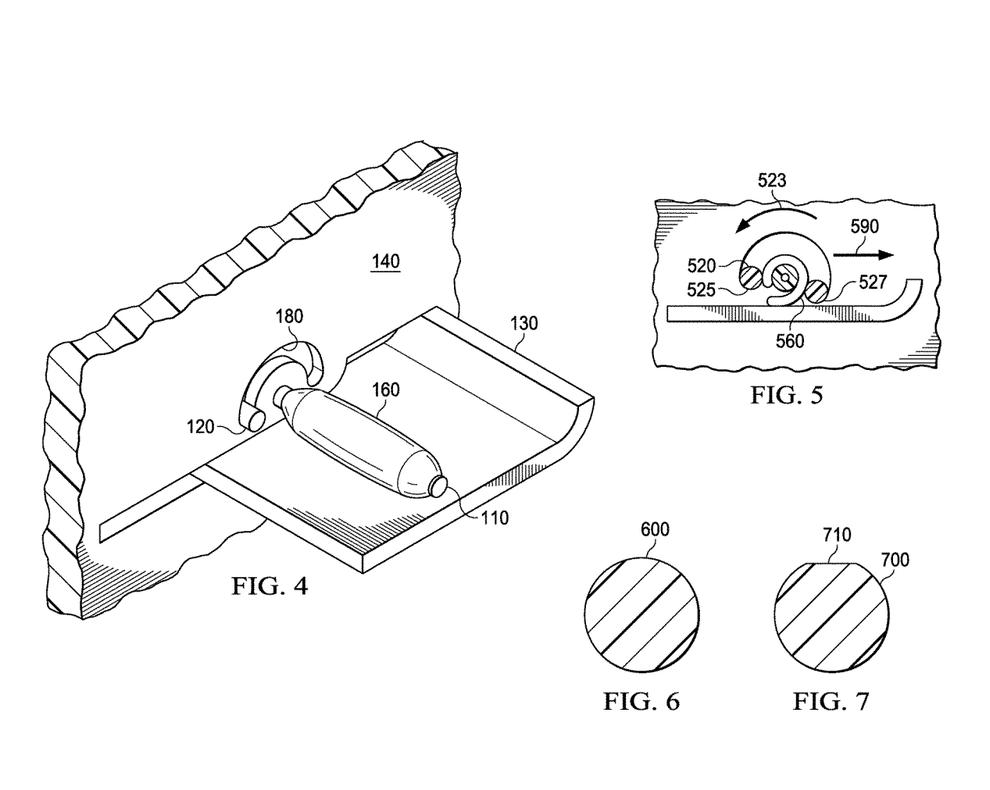
FIG. 4 shows a detail view of a portion of another example intraocular lens folding device.
FIG. 5 shows a partial front view of another example intraocular lens folding device.
FIGS. 6 and 7 show cross-sectional views of example folding pins.

FIG. 4 shows fully folded IOL 160 on the folding pin 110. When the IOL 160 is fully folded, in some instances, the guide pin 120 may be refracted through the path 180. Thus, as shown in FIG. 4, the guide pin 120 is in a refracted position. With the guide pin 120 retracted, accessibility to the IOL 160 is improved, and the IOL 160 may be maintained in a folded configuration by being held between the folding pin 110 and stage 130.

FIG. 5 shows a portion of a folding device having a plurality of guide pins. When a first guide pin 520 rotates approximately 180°, a second guide pin 521 may be extended through the path 580. The second guide pin 521 maintains the IOL 560 against the folding pin 510 and/or against a portion of the IOL 560 as the folding process continues. With the second guide pin 521 extended, the first guide pin 520 may be retracted through the path 580. As the folding process continues, the folding pin 510 and second guide pin 521 may continue to rotate in the direction of arrow 523 and stage 530 may continue to move in the direction of arrow 590. This process of retracting a guide pin at end position 525 and extending a guide pin at starting position 527 may continue an indefinite number of times and conclude once the IOL 560 is completely folded. In some instances, the first guide pin 520 may rotate more or less than 180° prior to being retracted. Also, in some instances, the second guide pin 521 may be extended when the first guide pin 520 rotates more or less than 180°.

FIGS. 6 and 7 show example cross-sectional shapes for a folding pin, such as folding pins 110 and 410. Particularly, FIGS. 6 and 7 illustrate example folding pins 600 and 700, respectively. FIG. 7 shows a circular cross-sectional shape. FIG. 6 shows a substantially circular cross-sectional shape with a flat surface 710 formed therein. The flat surface 710 may provide an improved hold on an IOL. For example, the flat surface 600 may provide for an improved hold of the IOL during an initial part of a folding process.

Figure 8:
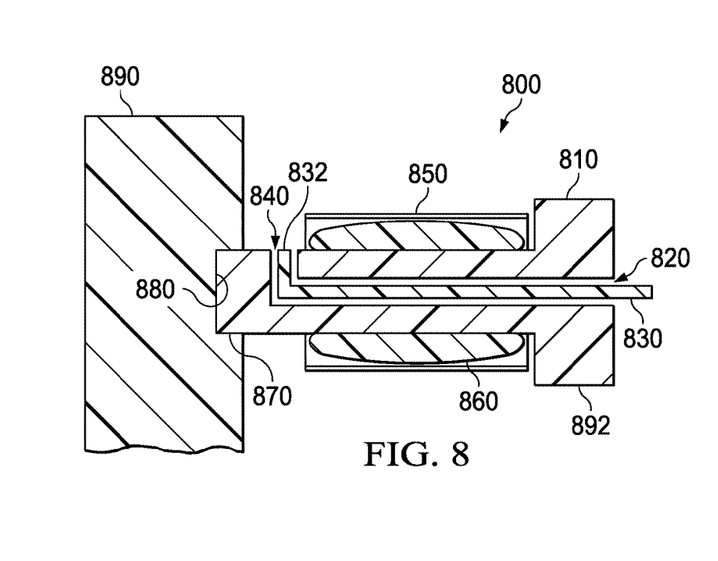
FIG. 8 shows a cross-sectional view of a portion of an example intraocular lens folding device with a removable folding pin.

FIG. 8 shows an example device 800 that includes an example folding pin 810. Example folding pin 810 may be similar to one or more of the folding pins described herein, such as, folding pins 110, 600, and 700. Folding pin 810 includes a passage 820, and a retention member 830 extending through the passage 820. The retention member 830 may be extended or retracted within the passage 820 such that a distal end 832 of the retention member 830 is extended from or refracted into a distal opening 840 of the passage 830. A folded IOL 860 is disposed on the folding pin 810. The retention member 830, in an extended position, assists in retaining the folded IOL 860 on the folding pin 810. Particularly, the retention member 830 prevents the folded IOL 860 from moving distally on the folding pin 810. Consequently, the retention member 830 in the extended position permits retention of the folded IOL 860 between the time when the IOL 860 is folded until the time when the IOL 860 is ready to be inserted into an eye.

A binding member 850 may be utilized to hold the IOL 860 within a folded configuration. For example, in some instances, the binding member 850 may be sleeve. In some instances, the binding member may be an adhesive tape. In some instances, the binding member 850 may be an adhesive or glue. In some implementations, the binding member 850 may be formed form a biocompatible polymer.

In some implementations, a folding pin may be detachable from an IOL folding device. FIG. 8 shows a distal end 870 of the folding pin 810 removeably received into a receptacle 880 formed in a back 890 of the device 800. The folding pin 810 may be removed from the receptacle 880. Particularly, with the IOL 860 folded on the folding pin 810, the folding pin 810 may be removable from the receptacle 880.

A proximal end 892 of the folding pin 810 may be coupleable to an insertion instrument, discussed in more detail below. The insertion tool may be used to remove the folding pin 810 from the receptacle 880.

Figure 9:
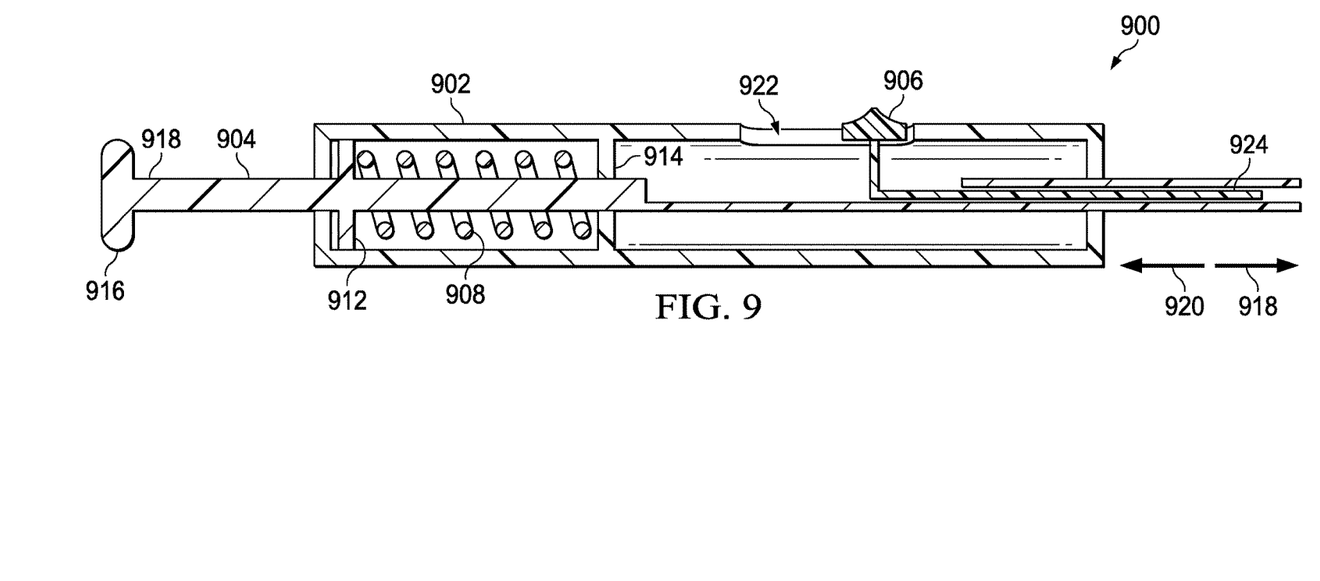
FIG. 9 shows a cross-sectional view of an example intraocular lens implantation device.

FIG. 9 shows an example implantation instrument 900. The instrument 900 includes a housing 902 and a plunger 904 extending through the housing 902. The instrument 900 may also include a biasing member 908 disposed within a cavity 1010 formed in the body 902. The biasing element 908 may be disposed between a first flange 912 formed on the plunger 904 and a shoulder 914 formed by the housing 902. The plunger 904 may also include a second flange 916 formed at a proximal end 918. A user may apply a force to the second flange 916 to displace the plunger 904 longitudinal relative to the housing 902 in the direction of arrow 918. This displacement of the plunger 904 causes the biasing member 908 to compress. When the applied force is removed, the biasing member 908 urges the plunger 904 to move in the direction of arrow 920. In some instances, the biasing member 908 may be a spring. In some implementations, the biasing member 908 may be a coil spring.

The instrument 900 may also include an actuator 906. In the illustrated example, the actuator 906 is slideable within a slot 922 formed in the housing 902. A user's thumb or other finger may be used to extend and retract the actuator 906 within slot 922. The actuator 906 may include a coupling member 924 that extends through a passage 926 formed in the plunger 904. The coupling member 924 is configured to couple to the retention member of a folding pin, such as retention member 803 of folding pin 810.

Figure 10:
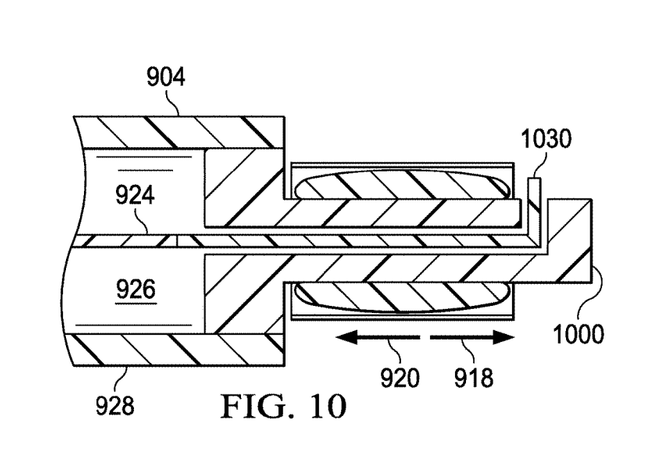
FIG. 10 shows a detail, cross-sectional view of a distal end of the implantation device of FIG. 9 with a folding pin coupled thereto.

FIG. 10 shows a detail cross-sectional view of a distal end of the plunger 904 of the instrument 900 with a folding pin 1000 coupled therewith. The folding pin 1000 is received into the passage 926 at a distal end 928 of the plunger 904. The folding pin 1000 may be similar to folding pin 810. The instrument 900 and the folding pin 1000 may be coupled to each other in numerous ways. For example, the instrument 900 and folding pin 1000 may be coupled with a threaded connection, an interference fit, a combination of both a threaded connection and interference fit, a detent connection, or a protrusion received into a slot, to name a few, non-limiting examples. Retention member 1030 may be releaseably couple to the coupling member 924. Thus, a longitudinal movement of the coupling member 924 results in a corresponding movement of the retention member 1030.

Displacement of the actuator 906 in the direction of arrow 920 results in displacement coupling member 924 and the retention member 1030 in the direction of arrow 920. Sufficient displacement in the direction of arrow 920 causes the distal end 1032 of the retention member 1030 to be refracted into passage 1020 through distal opening 1040 of the passage 1020. With the retention member 1030 retracted, the folded IOL 1060 may be easily removed from the folding pin 1010. Particularly, the folded IOL 1060 may be slid along the folding pin 1010 in the direction of arrow 918.

With the folding pin 1010 coupled to the instrument 900, a distal end of the instrument 900 may be inserted into an eye, such as by insertion through a wound formed in the eye. Once the folded IOL 1060 is positioned at a desired location within the eye, the retention member 1030 may be retracted and the folded IOL 1060 may be removed from the folding pin 1010 and implanted into the eye. The folded IOL 1060 may be slid off of the folding pin 1010 at a desired location in the eye, and the instrument 900 and folding pin 1010 combination may be withdrawn from the eye.

A binding member 1050 may be removed from the IOL 1060 once the IOL 1060 is at the desired location in the eye. For example, the binding member 1050 may be removed with the use of another instrument inserted into the eye. Forceps, tweezers, or other types of grasping instruments may be utilized to remove the binding member 1050 from the folded IOL 1060. The binding member 1050 may be removed from the eye. Once the binding member 1050 is removed from the folded IOL 1060, the IOL 1060 may naturally begin to expand and occupy the intended location within the eye. A position of the unfolded IOL 1060 may be manipulated by a user, such as with the use of an instrument inserted into the eye.

Figure 11:
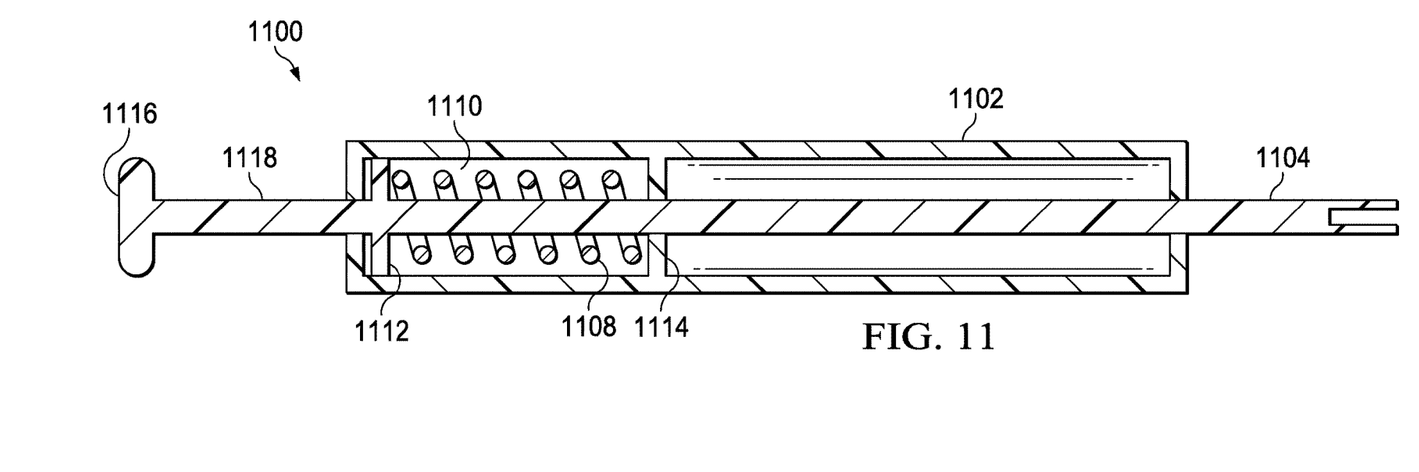
FIG. 11 shows a cross-sectional view of another example intraocular lens implantation device.

FIG. 11 shows another example implantation instrument 1100. The instrument 1100 may be similar to the instrument 1000 except that instrument 1100 does not include an actuator. The instrument 1100 includes a housing 1102 and a plunger 1104 received within the housing 1102. The instrument 1100 may also include a biasing member 1108 disposed within a cavity 1110 formed in the housing 1102. The biasing element 1108 may be disposed between a first flange 1112 formed on the plunger 1104 and a shoulder 1114 formed by the housing 1102. The plunger 1104 may also include a second flange 1116 formed at a proximal end 1118. A user may apply a force to the second flange 1116 to displace the plunger 1104 longitudinal relative to the housing 1102 in the direction of arrow 1118. This displacement of the plunger 1104 causes the biasing member 1108 to compress. When the applied force is removed, the biasing member 1108 urges the plunger 1104 to move in the direction of arrow 1120. In some instances, the biasing member 1108 may be a spring. In some implementations, the biasing member 1108 may be a coil spring.

Figure 12:
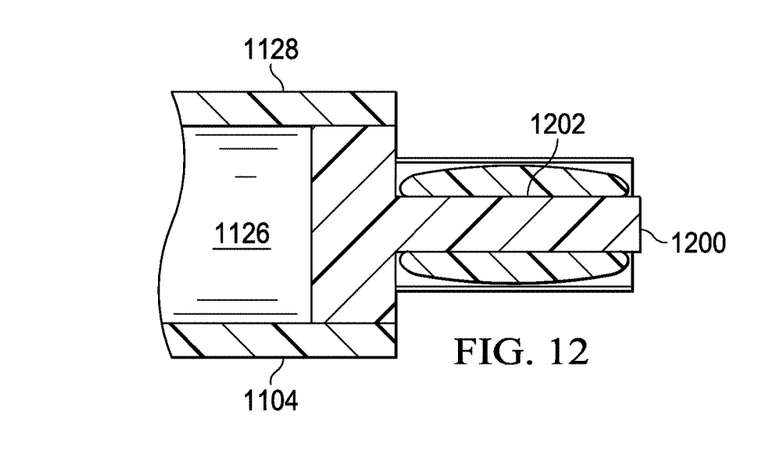
FIG. 12 is a detail, cross-sectional view of a distal end of the implantation device of FIG. 11 with a folding pin coupled thereto.

FIG. 12 is a detail cross-sectional view of the distal end 1128 of the plunger 1104 of instrument 1100. A folding pin 1200 is coupled to the plunger 1104 of the plunger 1104. Particularly, a portion of the folding pin 1200 is received into a bore 1126 formed in the distal end 1128. The folding pin 1200 may be similar to folding pins 810 and 1000, except that folding pin 1200 excludes a feature extending through a passage formed in the folding pin 1200. In some instances, the folding pin 1200 includes a shaft 1202 that has a constant diameter along a length thereof. In other instances, the folding pin 1200 may include a retaining feature.

Figure 13:
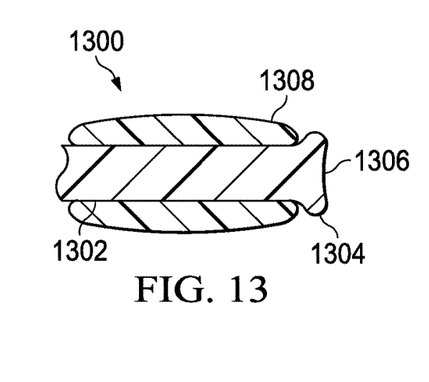
FIG. 13 is a detail, cross-sectional view of a distal end of an example folding pin.

FIG. 13 shows another example folding pin 1300 that includes a shaft 1302 and a retaining feature 1304 formed on the shaft 1302. The retaining feature 1304 may be formed at a distal end 1306 of the pin 1302. A folded IOL 1308 disposed on the shaft 1302 may be retained on the folding pin 1300 by the retaining feature 1304 prior to implantation. When implantation of the IOL 1308 is desired, the IOL 1308 may be slid distally along the shaft 1302 over the retaining feature 1304. In some instances, the retaining feature 1304 may be compliant and fold inwardly to permit removal of the IOL 1308 from the folding pin 1300. In some instances, the retaining feature 1304 may be an annular flange. In other instances, the retaining feature may be one or more protrusions extending from the shaft 1302.

Figures 14, 15:
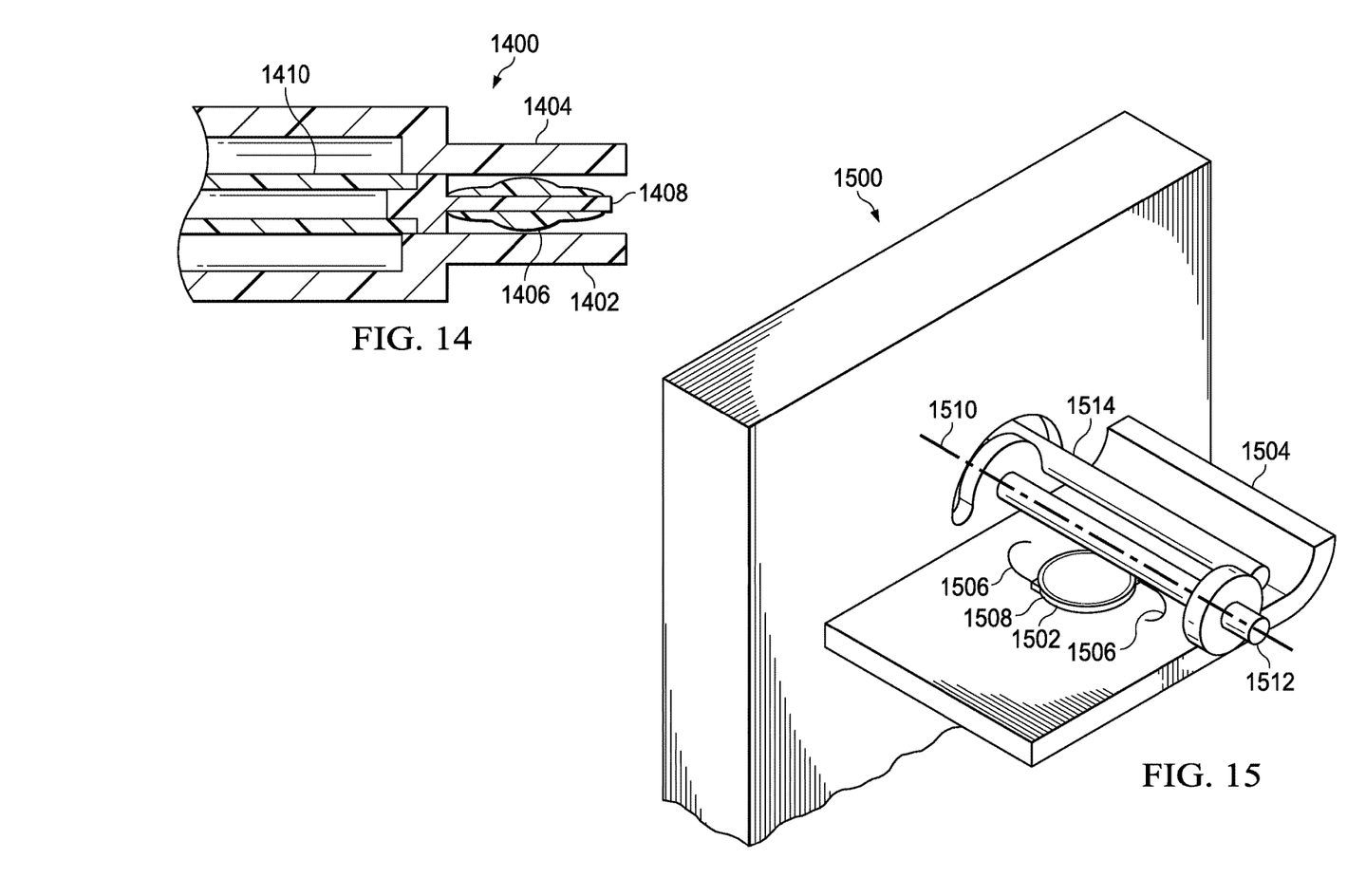
FIG. 14 is a detail, cross-sectional view of another example intraocular lens implantation device.
FIG. 15 is a perspective view of a portion of an intraocular lens folding device.

FIG. 14 shows another example implantation instrument 1400. The instrument 1400 may be similar to either of instruments 900 or 1100. However, the instrument 1400 may include a tubular portion 1402 disposed at a distal end 1404. The tubular portion 1402 is configured to receive a folded IOL 1406. For example, the folded IOL 1406 may be disposed in the tubular portion 1402 prior to implantation in an eye.

A plunger 1410 of the instrument 1400 may be extended to be coupled to folding pin 1408. As shown in FIG. 14, the folding pin 1408 includes IOL 1406 thereon. The plunger 1410 may then be retracted so that the folded IOL 1406 is housed within the tubular portion 1402. The tubular portion 1402 may then be inserted into a wound formed in the eye. The plunger 1410 may be extended to position the folded IOL 1406 at a desired location within the eye. Particularly, the plunger 1410 may be extended from the instrument 1400 such that the folded IOL 1406 is moved out of the tubular portion 1402. The IOL 14006 may then be removed from the folding pin 1408 and deposited in the eye.

FIG. 15 shows another example IOL folding device 1500. The IOL folding device 1500 may be similar any of the other IOL folding device described herein. An example, unfolded IOL 1502 disposed on a stage 1504. In the example shown, the IOL 1502 is oriented such that haptics 1506 extending from an optics portion 1508 of the IOL 1502 are aligned with a longitudinal axis 1510 of folding pin 1512. A guide pin 1514 is shown adjacent to the folding pin 1512. The IOL 1502 may be folded in this orientation. By being folded in the described orientation, the folding of the haptics 1506 may be better controlled as well as reduce an overall size of the IOL 1502 when fully folded.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. An intraocular lens folding system comprising:
   a folding device comprising:
   a body;
   a folding pin mounted to the body, the folding pin comprising a first longitudinal axis;
   a guide pin mounted to the body adjacent to the folding pin, the guide pin comprising a second longitudinal axis offset from the first longitudinal axis, the guide pin rotatable on the body about a longitudinal axis of the folding pin; and
   a stage mounted to the body adjacent to the folding pin, the stage laterally moveable relative to the folding pin.

2. The intraocular lens folding system of claim 1, wherein the folding pin is rotatable relative to the body about the longitudinal axis.

3. The intraocular lens folding system of claim 1, wherein the folding pin is removable from the body.

4. The intraocular lens folding system of claim 1, wherein the guide pin and folding pin are configured to rotate synchronously.

5. The intraocular lens folding system of claim 1, wherein a rate at which the guide pin rotates and the rate at which the folding pin rotates is the same.

6. The intraocular lens folding system of claim 1, wherein lateral movement of the stage is synchronized with the rotation of the guide pin.

7. The intraocular lens folding system of claim 1, wherein a speed of the lateral movement of the stage is the same as a tangential velocity of the guide pin.

8. The intraocular lens folding system of claim 1 further comprising an insertion device, the insertion device comprising:
   a housing; and
   a plunger moveable within the housing, a distal end of the plunger configured to receive at least a portion of the folding pin.

* * * * *